(12) United States Patent
Visser et al.

(10) Patent No.: US 8,691,311 B2
(45) Date of Patent: *Apr. 8, 2014

(54) TASTE IMPROVING SUBSTANCES

(75) Inventors: Jan Visser, Hulzen (NL); Harry Renes, Lelystad (NL); Esther Van Ommeren, Lelystad (NL); Sander Tondeur, Loosdrecht (NL); Chris Winkel, Bussum (NL)

(73) Assignee: Givaudan Nederland Services B.V., Naarden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/605,279

(22) Filed: Sep. 6, 2012

(65) Prior Publication Data

US 2012/0328536 A1 Dec. 27, 2012

Related U.S. Application Data

(63) Continuation of application No. 11/800,417, filed on May 4, 2007, now Pat. No. 8,263,161.

(30) Foreign Application Priority Data

May 5, 2006 (EP) .................................. 06113546.3

(51) Int. Cl.
*A23L 1/22* (2006.01)

(52) U.S. Cl.
USPC ........................................................ 426/534

(58) Field of Classification Search
USPC ........................................................ 426/534
See application file for complete search history.

(56) References Cited

U.S. PATENT DOCUMENTS

| | | | |
|---|---|---|---|
| 5,753,708 | A | 5/1998 | Koehler et al. |
| 6,287,620 | B1 | 9/2001 | Van Den Ouweland et al. |
| 2004/0072254 | A1 | 4/2004 | Callamaras et al. |
| 2005/0013846 | A1 | 1/2005 | Pelan et al. |
| 2005/0266031 | A1 | 12/2005 | Dickerson et al. |

FOREIGN PATENT DOCUMENTS

| | | |
|---|---|---|
| EP | 1 291 342 | 3/2003 |
| GB | 1 420 909 | 1/1976 |
| GB | 2 396 414 | 6/2004 |
| WO | 90/06689 | 6/1990 |
| WO | 92/06601 | 4/1992 |
| WO | 97/04667 | 2/1997 |
| WO | 01/77292 | 10/2001 |
| WO | 01/93692 | 12/2001 |
| WO | 02/096464 | 12/2002 |
| WO | 02/100192 | 12/2002 |
| WO | 2004/055048 | 7/2004 |
| WO | 2004/075663 | 9/2004 |
| WO | 2005/102071 | 11/2005 |

OTHER PUBLICATIONS

Merriam-Webster.com/dictionary/beverage,"Definition of Beverage" viewed Aug. 27, 2011.
Sidel'Kowskaja G. et al; Beilstein Institute for Organic Chemistry, Frankfurt-Main, DE; XP002407539; Database accession No. 34633; Izv. Akad. Nauk SSSR Ser. Khim., 1958, pp. 1111-1114.
Fischer G. et al; Beilstein Institute for Organic Chemistry, Frankfurt-Main, DE; XP002407540; Database accession No. 906438; Tetrahedron, 1971, pp. 5683-5696. vol. 27, Issue 22.
Nagase O. et al; Beilstein Institute for Organic Chemistry, Frankfurt-Main, DE; XP002407541; Database accession No. 922406; Chem. Pharm. Bull., No. 17, 1969, pp. 398-399.
Lindemann, Bernd; "Receptors and Transduction in Taste"; Nature, Sep. 13, 2001, pp. 219-225, vol. 413.
Hideyuki Suzuki et al, "Improvement of the Bitter Taste of Amino Acids Through the Transpeptidation Reaction of Bacterial Glutamyltranspeptidase", J. Agric. Food Chem., 2002, pp. 313-318, vol. 50.
Keigo Shima et al, "Novel Brothy Taste Modifier Isolated From Beef Broth", J. Agric. Food Chem., 1998, pp. 1465-1468, vol. 46.
Yoichi Ueda, et al, "Flavor Characteristics of Glutathione in Raw and Cooked Foodstuffs", Biosci. Biotech. Biochem., 1997, pp. 1977-1980, vol. 61, No. 12.
Alexey N. Pronin, et al, "Identification of Ligands for Two Human Bitter T2R Receptors", Chem. Senses, 2004, pp. 583-593, vol. 29.

(Continued)

*Primary Examiner* — Elizabeth Gwartney
(74) *Attorney, Agent, or Firm* — The Webb Law Firm

(57) ABSTRACT

The present invention relates to taste improvement of foodstuffs, beverages, tobacco products and oral care products, using a substance according to formula (I), edible salts or edible esters thereof:

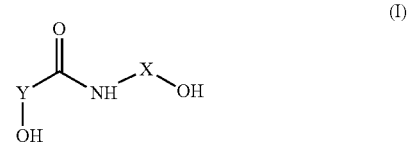

(I)

It was found that substances represented by formula (I) are capable of modifying and complementing, the sensory impact of taste imparting substances. Thus, the present taste improving substances are advantageously applied in flavor compositions, foodstuffs, tobacco products and oral care products. Typical examples of taste improving substances according to the present invention include N-(2-hydroxyethyl) 3-hydroxypropionamide; N-(2-hydroxyethyl) 3-hydroxybutyramide; N-(2-hydroxyethyl) 4-hydroxybutyramide; N-(2-hydroxyethyl) N-5-hydroxypentanoylamide; N-(2-hydroxyethyl) 4-hydroxypentanoylamide; N-(2-hydroxyethyl) 3-hydroxypentanoylamide; N-(2-hydroxyethyl) 2-methyl-4-hydroxy-butyramide; N-(2-hydroxyethyl) 2-methyl-3-hydroxybutyramide; N-(2-hydroxyethyl) N-6-hydroxyhexanoylamide; N-(2-hydroxyethyl) 5-hydroxyhexanoylamide; N-(2-hydroxyethyl) 4-hydroxyhexanoylamide; N-(2-hydroxyethyl) 3-hydroxyhexanoylamide; N-(2-hydroxyethyl) 4-hydroxy-2-keto-3-methyl-pentanoylamide; N-(2-hydroxyethyl) 4-hydroxy-2-keto-3-methyl-hexanoylamide and mixtures thereof.

16 Claims, No Drawings

(56) References Cited

OTHER PUBLICATIONS

Margaret Cliff et al, "Descriptive Analysis of Oral Pungency", J. of Sensory Studies, 1992, pp. 279-290, vol. 7.

Dalton, P. et al, "The Merging of the Senses: Integration of Subthreshold Taste and Smell", Nature Neuroscience, May 2000, pp. 431-432, vol. 3, No. 5.

Breslin, Paul A.S. et al, "Interactions Among Salty, Sour and Bitter Compounds", Trends in Food Science & Technology, Dec. 1996, pp. 390-399, vol. 7.

Shostakovskii, M.G. et al, "Investigation of Lactones and Lactams: Communication 11. Condensation of Ethylene Oxide with Lactams", N. D. Zelinskii Instutute of Organic Chemistry of the Academy of Sciences of the USSR, Jul. 26, 1957, pp. 109-111.

TASTE IMPROVING SUBSTANCES

CROSS REFERENCE TO RELATED APPLICATIONS

This application claims priority as a continuation of U.S. patent application Ser. No. 11/800,417, filed May 4, 2007, which claims priority to European Patent Application No. 06113546.3, filed May 5, 2006, the entire contents of each of which are expressly incorporated by reference.

FIELD OF THE INVENTION

The present invention concerns taste improvement in foodstuffs, beverages, tobacco products and oral care products. More particularly, the present invention provides flavour compositions that can be used to confer a fuller and richer taste to foodstuffs, beverages, pharmaceutics, tobacco products and oral care products. The flavour compositions according to the invention are characterised by the presence of one or more substances that are capable of modifying and complementing the impact of other flavour imparting substances.

The present invention also encompasses the use of the aforementioned taste improving substances for improving the taste of foodstuffs, beverages, tobacco products and oral care products, as well as to foodstuffs, beverages, tobacco products and oral care products containing these substances.

BACKGROUND OF THE INVENTION

The flavour of foodstuffs and beverages consists of two parts: the aroma and the taste. In general what is perceived through the olfactory epithelium in the nasal cavity is referred to as 'aroma', whereas the term 'taste' is generally used to describe the sensory impact that is perceived via the mouth, especially the tongue. The flavour sensation experienced upon consumption, especially the taste, provides the final analysis of food prior to ingestion thereof. Visual and olfactory (smell) signals already give a first indication but only after intake of the food into the mouth the final decision is made either to ingest or to reject the food. Sweet taste is usually a signal that the food is safe (appetising) leading to ingestion of the food. The 'reactions' to salt and umami are really dependent on the strength of the signal. Bitter and sour are usually experienced as repulsive taste sensations that can lead to rejection. Temperature is another measure by which the food is judged just as well as aching sensations like capsaicin (hot pepper) and certain chemicals (like carbon dioxide).

In short, this means that taste is a very important and very complex system. Until recently most flavour research was focused towards aroma. Especially the last years a series of publications relating to molecules with a (positive) contribution to the taste of foodstuffs has emerged.

Such research has been stimulated significantly by the fact that quite some receptors which are involved in the different taste sensations have been characterized by now (B. Lindemann; Nature 413, 219 (2001)).

Another interesting aspect of taste is that it can have an impact on aroma. It was reported that people having artificially sweetened water in their mouth were significantly more sensitive to the smell of benzaldehyde than people having plain water in their mouth (P. Dalton et al, Nature Neurosci. 3, 431-432 (2000)).

Several screening systems have been described that make it possible to screen, in a short time, large series of molecules for their (modulating) effect on taste response (cf. WO04055048, GB2396414, WO0177292 and US2004/0072254).

Most research on taste modulation so far has been devoted to taste enhancement in savoury products. Several, mainly Japanese, publications describe umami molecules, i.e. alternatives to mono sodium glutamate (MSG) (H Suzuki et al, J Agric Food Chem 50, 313-318 (2002); K Shima et al, J Agric Food Chem 46, 1465-1468 (1998); Y Ueda et al, Biosc Biotech Biochem 61 1977 (1997)).

In EP 1291342, a 'general taste enhancer' is disclosed that was reported to be suitable for enhancing sweetness as well.

In patent applications WO9704667 and WO04075663 tripeptides and amino acid condensates with lactic acid and succinic acid are described that have both their own taste as well as some enhancing properties. Alpha keto acids are reported to give body and mouthfeel to foodstuffs they are added to (U.S. Pat. No. 6,287,620).

Chlorogenic acids are claimed to enhance sweetness and to reduce bitterness (WO02100192).

Quite a bit of work has been devoted to find bitter taste suppressors (A. N. Pronin et al, Chemical Senses 29, 583-593 (2004); EP1401500; P. A. Breslin, Trends in Food Science & Technology 7, 390-399 (1996)).

In sweet and beverage products, further examples of the importance of the gustative dimension of flavourings have been reported. These examples include taste attributes such as bitterness, tingling and cooling-freshness.

Bitterness is an essential aspect of some food flavours, among which chocolate taste. Purine alkaloids, like theobromine and caffeine, as well as amino acids and peptides have been known for a long time as bitter substances. In British patent no. GB 1420909 it is disclosed that the bitter flavour of cocoa can be reproduced using a combination of a purine alkaloid and an amino acid or an oligopeptide which 'produces a surprisingly more natural simultaneously bitter and astringent flavour note than either of these types of substances alone'.

Menthol, an important constituent of peppermint oil, has a strong impact on flavoured products not only because of its mint smell but also because it imparts a cooling and fresh taste. Next to mint flavoured products, it has been suggested to employ menthol in other types of flavour to impart a cool taste. US patent application no. US2005013846 for example discloses how menthol and derivatives thereof can be used as flavouring in water continuous spreadable acidified food products to obtain table spreads exhibiting a fresh, cool taste impression.

Similarly, cinnamic aldehyde and eugenol, constituents of cinnamon oil, are used in flavouring composition for confectionery products, not only for their smell but also because they impart a warm and tingling taste. The oral pungency of cinnamic aldehyde was described as burning and tingling by Cliff M and Heymann H [Journal of Sensory Studies 7 (1992) 279-290]. According to the same authors eugenol exhibits a long-lasting numbing effect. Cinnamon oil has been proposed as a taste improving flavouring. International patent application no. WO9006689 discloses that cinnamon oil, among other spice extracts, added to a minty flavour formulation, can be used to improve the long-lasting flavour of chewing-gum.

There is still a need for new so-called flavour modulating substances that provide a positive contribution to the flavour, especially taste, of foodstuffs, beverages, pharmaceutics, tobacco products and oral care products they are incorporated in. One objective of the present invention therefore is to provide such substances and compositions comprising them.

SUMMARY OF THE INVENTION

The present inventors have surprisingly found that substances represented by the following formula (I) can be used advantageously to improve the taste of foodstuffs, beverages, tobacco products and oral care products:

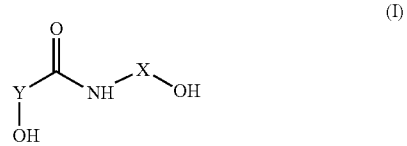

(I)

Therefore, the present invention relates to flavour compositions, foodstuffs, beverages, tobacco products and oral care products, comprising at least one substance according to formula (I).

Other aspects of the present invention relate to the use of said substances for improving the taste of foodstuffs, beverages, tobacco products and oral care products, and to a process for improving the taste of these products.

The taste improving substances according to the present invention can be applied advantageously to impart desirable taste attributes to the aforementioned products.

In addition, the present taste improving substances are capable of modifying the taste impact of other flavour ingredients contained within these same products, thereby improving the overall flavour quality of these products.

DETAILED DESCRIPTION OF THE INVENTION

Accordingly, the present invention in a first aspect relates to the use for improving the taste of foodstuffs, beverages, tobacco or oral care products of a substance according to formula (I), or edible salts thereof:

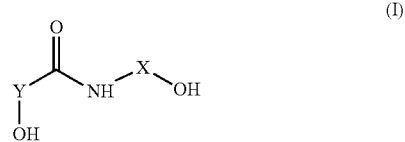

(I)

wherein:
X represents $C_1$-$C_3$ alkyl, optionally substituted with one or more substituents selected from methyl and hydroxyl;
and wherein Y represents linear $C_2$-$C_5$ alkylene or linear $C_2$-$C_5$ alkenylene, each optionally substituted with one or more substituents selected from the group of oxo, $C_1$-$C_5$ alkyl; and $C_1$-$C_5$ alkenyl, which $C_1$-$C_5$ alkyl and $C_1$-$C_5$ alkenyl each may optionally be substituted with one or more hydroxyl groups.

The present inventors have found that the above-mentioned substances are very useful flavour ingredients which, particularly in the presence of other flavouring substances, are capable of imparting highly appreciated taste sensations to the products in which they are incorporated, specifically "cooling", "pungent", "sharp", "hot" "tingling", "bite", "burning", "warm", "alcohol-like", "continuity", "complexity", "expanding", "salty", "umami" and/or "long lasting". Because of this, the present taste improving substances can be employed to improve the taste (including "mouthfeel") of foodstuffs, beverages, tobacco products and oral care products.

The taste improving substances of the present invention as such are capable of imparting highly desirable taste attributes. In addition, it has been found that the taste improving substances according to the invention are capable of complementing and modifying the sensory impact of other flavouring substances contained in the aforementioned products, including complementing and modulating "alcohol sensation", "bitterness", "hot taste sensation", "cold taste sensation", "carbonation effects", "umami" and/or "salt taste impact".

Throughout this document the terms "taste" and "flavour" are used interchangeably to describe the sensory impact that is perceived via the mouth, especially the tongue, and the olfactory epithelium in the nasal cavity. The term "taste modifying" as used herein refers to the capability of a composition or substance to alter the taste impact of other, flavour imparting, substances present within the same product, with the proviso that this change in taste impact is not caused by the flavour contribution of said composition or substance per se, but instead that it mainly results from the combined effect of on the one hand the taste improving composition or substance and on the other hand the other flavour imparting substances. The present substances combine the capability of modifying the taste of other flavour substances with a taste contribution of their own. The favourable impact of the present taste improving substances is believed to be the result of the combination of these two effects.

Because the taste improving substances according to the invention are not particularly volatile, they do not produce a strong aroma impact, even though they can affect the aroma impact of other flavour substances. Here the term "aroma" refers to the aspect of taste that is perceived through the olfactory epithelium. Because of the low volatility of the present taste improving substances it is believed that the advantageous properties of these substances are somehow associated with the impact that these substances have on the sensory receptors located within the mouth.

It was found that particularly satisfying results can be obtained with taste improving substances as defined herein before wherein X in formula (I) represents ethylene or propylene, optionally substituted with one or more substituents selected from hydroxyl and methyl; more preferably ethylene, optionally substituted with one or more substituents selected from hydroxyl and methyl. Most preferably X represents ethylene.

In a particularly preferred embodiment of the invention, Y in formula (I) represents linear $C_2$-$C_5$ alkylene or linear $C_2$-$C_5$ alkenylene, each optionally substituted with one or more substituents selected from the group of $C_1$-$C_5$ alkyl and $C_1$-$C_5$ alkenyl, each optionally be substituted with one or more hydroxyl groups.

In a still more preferred embodiment of the invention, Y represents linear $C_2$-$C_5$ alkylene or linear $C_2$-$C_5$ alkenylene, even more preferably $C_3$-$C_5$ alkylene or $C_3$-$C_5$ alkenylene, each optionally substituted with one or more substituents selected from methyl, ethyl and propyl. Most preferably Y represents $C_3$-$C_5$ alkylene optionally substituted with one or more substituents selected from methyl, ethyl and propyl.

In another particularly preferred embodiment of the invention, Y in formula (I) represents linear $C_2$-$C_5$ alkylene substituted with an oxygen atom and optionally further substituted with one or more substituents selected from of $C_1$-$C_5$ alkyl and $C_1$-$C_5$ alkenyl, each optionally be substituted with one or more hydroxyl groups. Even more preferably, Y represents linear $C_2$-$C_5$ alkylene, still more preferably $C_3$-$C_5$ alkylene, substituted with an oxygen atom; which alkylene is optionally further substituted with one or more substituents selected from methyl, ethyl and propyl. Yet, in an even more preferred embodiment Y represents linear $C_2$-$C_5$ alkylene substituted with an oxygen atom and a methyl group, said linear $C_2$-$C_5$ alkylene optionally being further substituted with one or more substituents selected from methyl, ethyl and propyl, most preferably from methyl and ethyl. Most preferably, the oxygen atom is attached to the carbon atom at the α-position relative to the amide moiety such that Y represents an optionally substituted $C_2$-$C_5$ α-keto-alkylene.

It will be clear to the skilled person that keto and enol forms of a carbonyl compound are tautomers existing in equilibrium with each other. Thus the aforementioned α-keto moiety will exist in equilibrium with the corresponding α-enol moiety under normal circumstances, i.e. under the circumstances that the present taste modulating substances will normally be used.

Hence, suitable examples of taste modulating substances represented by the aforementioned formula (I), that are particularly preferred for use in accordance with the invention include N-(2-hydroxyethyl) 3-hydroxypropionamide; N-(2-hydroxyethyl) 3-hydroxybutyramide; N-(2-hydroxyethyl) 4-hydroxybutyramide; N-(2-hydroxyethyl) N-5-hydroxypentanoylamide; N-(2-hydroxyethyl) 4-hydroxypentanoylamide; N-(2-hydroxyethyl) 3-hydroxypentanoylamide; N-(2-hydroxyethyl) 2-methyl-4-hydroxy-butyramide; N-(2-hydroxyethyl) 2-methyl-3-hydroxybutyramide; N-(2-hydroxyethyl) N-6-hydroxyhexanoylamide; N-(2-hydroxyethyl) 5-hydroxyhexanoylamide; N-(2-hydroxyethyl) 4-hydroxyhexanoylamide; N-(2-hydroxyethyl) 3-hydroxyhexanoylamide; N-(2-hydroxyethyl) 4-hydroxy-2-keto-3-methyl-pentanoylamide; and N-(2-hydroxyethyl) 4-hydroxy-2-keto-3-methyl-hexanoylamide.

As used herein the term 'edible esters thereof' encompasses any edible derivative of the present flavour modulating substances and an acid formed by reaction of said acid with one of the hydroxyl groups present in said flavour modulating substance. Typically said acid is an organic acid such as a substituted or non-substituted, linear or branched $C_1$-$C_6$ carboxylic acid, more preferably a $C_1$-$C_4$ carboxylic acid, most preferably a $C_1$-$C_3$ carboxylic acid, or alternatively an inorganic acid such as phosphoric acid. Such esters will at least to a certain degree, possess some of the flavour characteristics of the corresponding substance according to formula (I) that is not esterified.

According to a preferred embodiment the present flavour modulating substance is selected from the group of substances represented by formula (I) as defined herein before and salts thereof.

In another particularly preferred embodiment, the aforementioned composition is a flavour composition comprising, based on the total (dry) weight of the composition, at least 0.1 wt %, more preferably at least 0.5 wt %, most preferably at least 1 wt %, of one or more flavouring substances and at least 0.001 wt. %, preferably at least 0.01 wt. %, of one or more of the present flavour modulating substances. Most preferably, the flavour composition contains at least 0.1 wt % of the present flavour modulating substances. Preferably the amount of the present flavour modulating substances does not exceed 80 wt %, more preferably it does not exceed 40 wt %. As used herein, the term "flavouring substance", refers to any substance that is not represented by formula (I) and that is capable of imparting a detectable flavour impact, especially at a concentration below 0.1 wt. %, more preferably below 0.01 wt. %. Typically, the present flavouring substances belong to one or more of the chemical classes of alcohols, aldehydes, ketones, esters, ethers, acetates, nitriles, terpene hydrocarbons, nitrogenous or sulphurous heterocyclic compounds and essential oils, and said flavouring substances can be of natural or synthetic origin. Many of these are listed in reference texts such as the book by S. Arctander (Perfume and Flavor Chemicals, 1969, Montclair, N.J., USA), or its more recent versions, or in other works of a similar nature, as well as in the abundant patent literature in the field of flavours.

Typically, in the present flavour composition, the one or more flavour modulating substances and the one or more flavouring substances as defined herein before are employed in a weight ratio within the range of 10:1 to 1:100, preferably in a weight ratio of 5:1 to 1:50.

The flavour composition according to the present invention may suitably be prepared in the form of a liquid, a paste or a powder. Flavour compositions according to the present invention preferably comprise at least one edible/food grade carrier, examples of which include maltodextrin, modified starch, gum arabic, propylene glycol and ethanol. In a particularly preferred embodiment the flavour composition is a free flowing powder.

Preferred examples of flavour compositions according to the present invention include sweet flavouring compositions, comprising one or more of the present flavour modulating substances and at least one flavouring substance that is typically used in sweet flavour applications, more particularly in the field of dairy, beverage and/or confectionery, still more preferably a flavouring substance that is commonly used in the field of flavouring alcoholic beverages, carbonated and still beverages.

In another preferred embodiment the present composition is a product selected from foodstuffs, beverages, tobacco products and oral care products, said product comprising at least 0.1 ppm, more preferably at least 1 ppm, still more preferably at least 5 ppm, most preferably at least 10 ppm of the present flavour modulating substances as defined herein before. Typically, the aforementioned products will contain the flavour modulating substances in a concentration of not more than 1000 ppm, preferably of not more than 500 ppm, most preferably of not more than 250 ppm. The present product will furthermore comprise one or more flavouring substances as defined herein before and/or other flavour imparting substances.

Typical examples of said products include alcoholic beverages, carbonated beverages, still beverages, yoghurts, ice creams, desserts, confectioneries, sweet snacks, seasonings, sauces, stocks, soups and dressings. The benefits of the present invention may also be realised in oral care products such as toothpaste and mouthwash, and in tobacco products, which includes any type of tobacco product for smoking as well as for non-smoking applications. It is noted that tobacco-like products are available for both smoking and non-smoking applications. The use of the present taste improving substances in these tobacco substitutes is also encompassed by the present invention.

Preferably the present product is selected from the group of foodstuffs, beverages and tobacco products, even more preferably from the group of foodstuffs and beverages.

Preferably the present product is selected from the group of alcoholic beverages, carbonated beverages, still beverages, yoghurts, ice creams, desserts, confectionery products, mouthwashes and toothpastes.

According to another particularly preferred embodiment the foodstuff or beverage is an alcoholic foodstuff or an alcoholic beverage. As used herein, the term 'alcoholic foodstuff or alcoholic beverage' refers to foodstuffs or beverages comprising ethanol, preferably in an amount of at least 0.5 wt %. More preferably said foodstuff or beverage comprises less than 50 wt % of ethanol, still more preferably less than 40 wt % of ethanol, still more preferably it comprises 2-30 wt %, most preferably 2-20 wt % of ethanol. Thus foodstuffs and beverages are provided by the present invention comprising at least 0.5 wt % of ethanol and at least 0.01 ppm of a flavour modulating substance as defined herein before.

Another aspect the present invention relates to a process of improving the flavour of a product selected from foodstuffs, beverages, tobacco products and oral care products, said process comprising incorporating into said product one or more flavour modulating substances as defined herein before, in an amount of at least 0.1 ppm, preferably of at least 1 ppm, most preferably at least 5 ppm. Preferably said amount does not exceed 1000 ppm, more preferably it does not exceed 500 ppm, still more preferably it does not exceed 250 ppm.

Still another aspect of the invention relates to the use of the flavour modulating substances as defined herein before for improving the flavour of a product selected from foodstuffs, beverages, tobacco products and oral care products. A preferred embodiment relates to the use of the present flavour modulating substances, as defined herein before, for mimicking and/or boosting ethanol sensation in foodstuffs or beverages, preferably, as mentioned herein before, in foodstuffs or beverages, comprising at least 0.5 wt % of ethanol. According to a preferred embodiment the present invention encompasses the use of the present flavour modulating substances, as defined herein, in an amount of between, 0.1-1000 ppm, more preferably 1-500 ppm.

Another embodiment of the invention relates to the use of the flavour modulating substances as defined herein before for imparting and/or modulating hot and/or cold taste sensation in the aforementioned products.

Yet another aspect of the present invention relates to processes of preparing flavour modulating substances, preferably flavour modulating substances as defined herein before.

According to one embodiment, said process comprises reacting a lactone represented by the following formula (III) or a salt or ester thereof with an amine represented by the following formula (IV) or a salt or ester thereof:

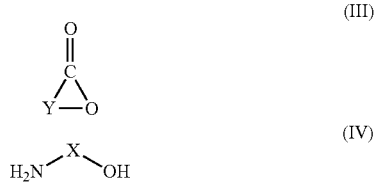

wherein:
X represents $C_1$-$C_3$ alkyl, optionally substituted with one or more substituents selected from methyl and hydroxyl; and wherein Y' represents linear $C_2$-$C_5$ alkylene or linear $C_2$-$C_5$ alkenylene, each optionally substituted with one or more substituents selected from the group of hydroxyl, provided that said hydroxyl group is a part of an enol moiety, $C_1$-$C_5$ alkyl; and $C_1$-$C_5$ alkenyl, which $C_1$-$C_5$ alkyl and $C_1$-$C_5$ alkenyl each may optionally be substituted with one or more hydroxyl groups. Although, as mentioned herein before, enol and keto moieties are tautomers normally existing in equilibrium with each other, in the present lactones the enol-form will be energetically favoured over the keto-form.

Preferably the present reaction is performed by heating to reflux said reactants in an organic solvent, such as toluene or pyridine, for a period of between 0.1-10 hours. According to a preferred embodiment, the reactants are used in a molar ratio of between 1:1-1:10. According to the present processes the reaction products are typically obtained as a precipitate and can be isolated by evaporating the solvent and optionally further purified using any of the techniques known by the skilled person, such as chromatography and crystallization.

The invention is further illustrated by means of the following examples.

EXAMPLES

Example 1

Stainless steel tubes, numbered 1-9, were filled with 15 g of ethanol and 2 g (=2 equivalents) of ethanolamine. To each tube 1 molar equivalent of one of the lactones as shown in table 1 was added. The tubes were closed and the mixture was heated for 5 hours at 70° C. After cooling, the content of each tube was transferred to a round-bottomed flask and ethanol and excess ethanolamine were removed by heating under vacuum (3 mbar, 160° C.).

The products were analyzed by NMR. The samples were about 90-95% pure amide derivatives of the hydroxy-acid and ethanolamine, with some unreacted lactone and some ethyl esters of the corresponding hydroxy-acids.

TABLE 1

| Tube: | Lactone used | Amount (g) |
|---|---|---|
| 1 | gamma-butyrolactone | 1.4 |
| 2 | gamma-valerolactone | 1.7 |
| 3 | delta-valerolactone | 1.7 |
| 4 | gamma-caprolactone | 1.9 |
| 5 | delta-caprolactone | 1.9 |
| 6 | delta-octalactone | 2.3 |
| 7 | delta-decalactone | 2.8 |
| 8 | delta-undecalactone | 3.0 |
| 9 | delta-dodecalactone | 3.3 |

Example 2

Two samples of fondant were prepared by mixing 65 Fondacreme (ex Belgosuc NV Belgium) with 35% sugar syrup (67° Brix). 2500 Ppm menthol was added as a 50% solution in propylene glycol. To a first sample (sample A), 50 ppm of N-(2-hydroxyethyl) 5-hydroxyhexanoyl amide (as prepared in example 1) was added. The second sample was the reference sample. The Samples were tasted by a professional panel.

Sample A gave more intense cooling than the reference sample. It is aggressive and its effect is immediate and through the whole oral cavity.

Example 3

Stainless steel tubes, numbered 10-20, were filled with 15 g of ethanol and 2 g (=2 equivalents) of ethanolamine. To each tube 1 molar equivalent of one of the lactones as shown in table 2 was added. The tubes were closed and the mixture was heated for 5 hours at 70° C. After cooling, the content of each tube was transferred to a round-bottomed flask and ethanol and excess ethanolamine were removed by heating under vacuum (3 mbar, 160° C.).

50 ppm of each one of the reaction products obtained was added to a different sample containing a solution of 0.6% NaCl and 0.03% MSG that had been prepared previously. These 11 samples and a reference solution of 0.6% NaCl and 0.03% MSG, were tasted by a professional panel.

TABLE 2

| Tube | Starting material |
|---|---|
| 10 | delta-caprolactone |
| 11 | β propiolactone |
| 12 | Ethyl 3-hydroxy-butyrate |
| 13 | γ butyrolactone |
| 14 | δ valerolactone |
| 15 | γ valerolactone |
| 16 | Ethyl 3-hydroxy-valerate |
| 17 | Ethyl 6-hydroxy-caproate |
| 18 | δ caprolactone |
| 19 | γ caprolactone |
| 20 | 5-ethyl-3-hydroxy-4-methyl-2(5H)-furanone (EHMF) |

All the Samples were judged to boost the (initial) salt impression compared with the reference solution.

Example 4

Two solutions of 0.6% NaCl and 0.03% MSG and 4 ppm pepper oleoresin (ex Warner Jenkinson, St Louis, USA) were prepared. To one sample (sample A), 50 ppm of N-(2-hydroxyethyl) 5-hydroxyhexanoyl amide (as prepared in example 1) was added. The other sample was used as the reference. Both samples were tasted by a professional panel.

In sample A the effect of initial hotness was increased and it gave more a hot, tingling after-taste, compared to the reference sample.

Example 5

Two solutions of 3% alcohol in water were prepared. To one sample (sample A), 50 ppm of N-(2-hydroxyethyl) 5-hydroxyhexanoyl amide (as prepared in example 1) was added. The other sample was used as the reference sample. Both samples were tasted by a professional panel.

Sample A had an alcohol-boosting effect and gave an aggressive alcohol impression in the whole oral cavity compared to the reference sample. Sample A tasted like a 5-6% ethanol water mixture.

Example 6

Commercially available Odol mouthwater (GlaxoSmithKline) was obtained from a local pharmacy and 4 solutions were prepared.

To a first sample (sample A), 50 ppm of N-(2-hydroxyethyl) 5-hydroxyhexanoyl amide (as prepared in example 1) was added. Samples A was tasted by a professional panel and compared with the mouthwater without added N-(2-hydroxyethyl) 5-hydroxyhexanoyl amide.

Sample A had a stronger overall impact than the mouthwater without added N-(2-hydroxyethyl) 5-hydroxyhexanoyl amide. It gave a more aggressive cooling in the whole oral cavity. Moreover sample A gave more initial cooling and more mouth-coating.

Example 7

Commercially available toothpaste was obtained from a local pharmacy and 4 samples of paste were prepared.

To a first sample (sample A), 50 ppm of N-(2-hydroxyethyl) 5-hydroxyhexanoyl amide (as prepared in example 1) was added and homogenized. Samples A was tasted by a professional panel and compared with the toothpaste without added N-(2-hydroxyethyl) 5-hydroxyhexanoyl amide.

Sample A had a stronger overall impact than the reference sample. It gave a more aggressive cooling in the whole oral cavity. Moreover sample A gave more initial cooling and more mouth-coating.

The invention claimed is:

1. A flavour composition comprising at least 0.1 wt. % of flavouring substances and from about 0.001 to 50 wt. % of one or more taste improving substances according to formula (I), edible salts thereof and/or edible esters thereof:

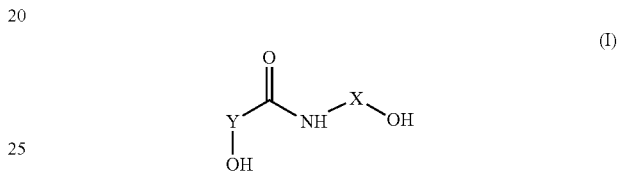

wherein:
X represents $C_1$-$C_3$ alkyl, optionally substituted with one or more substituents selected from methyl or hydroxyl;
and wherein Y represents linear $C_2$, $C_4$, or $C_5$ alkylene or linear $C_2$-$C_5$ alkenylene, each optionally substituted with one or more substituents selected from the group consisting of oxo, $C_1$-$C_5$ alkyl; and $C_1$-$C_5$ alkenyl, which $C_1$-$C_5$ alkyl and $C_1$-$C_5$ alkenyl each may optionally be substituted with one or more hydroxyl groups.

2. The flavour composition according to claim 1, wherein Y represents linear $C_2$, $C_4$, or $C_5$ alkylene or linear $C_2$-$C_5$ alkenylene, each optionally substituted with one or more substituents selected from the group consisting of $C_1$-$C_5$ alkyl and $C_1$-$C_5$ alkenyl, each optionally substituted with one or more hydroxyl groups.

3. The flavour composition according to claim 1, wherein Y represents an optionally substituted $C_4$ or $C_5$ alkylene or alkenylene.

4. The flavour composition according to claim 1, wherein Y represents a linear $C_2$, $C_4$, or $C_5$ α-ketoalkylene optionally substituted with one or more substituents selected from $C_1$-$C_5$ alkyl or $C_1$-$C_5$ alkenyl, each optionally substituted with one or more hydroxyl groups.

5. The flavour composition according to claim 4, wherein Y represents a linear $C_4$ or $C_5$ α-ketoalkylene optionally substituted with one or more substituents selected from methyl or ethyl.

6. The flavour composition according to claim 1, wherein X represents ethylene or propylene, optionally substituted with one or more substituents selected from hydroxyl or methyl.

7. The flavour composition according to claim 1, wherein the taste improving substance is selected from the group consisting of N-(2-hydroxyethyl) 3-hydroxypropionamide; N-(2-hydroxyethyl) N-5-hydroxypentanoylamide; N-(2-hydroxyethyl) 4-hydroxypentanoylamide; N-(2-hydroxyethyl) 3-hydroxypentanoylamide; N-(2-hydroxyethyl) N-6-hydroxyhexanoylamide; N-(2-hydroxyethyl) 5-hydroxyhexanoylamide; N-(2-hydroxyethyl) 4-hydroxyhexanoylamide; N-(2-hydroxyethyl) 3-hydroxyhexanoylamide; N-(2-hydroxyethyl) 4-hydroxy-2-keto-3-methyl-pentanoylamide; and N-(2-hydroxyethyl) 4-hydroxy-2-keto-3-methyl-hexanoylamide.

8. The flavour composition according to claim 1, comprising from about 0.01 to 10 wt. % of one or more taste improving substances according to formula (I), edible salts thereof and/or edible esters thereof.

9. The flavour composition according to claim 2, wherein Y represents an optionally substituted $C_4$ or $C_5$ alkylene or alkenylene.

10. The flavour composition according to claim 2, wherein X represents ethylene or propylene, optionally substituted with one or more substituents selected from hydroxyl or methyl.

11. The flavour composition according to claim 3, wherein X represents ethylene or propylene, optionally substituted with one or more substituents selected from hydroxyl or methyl.

12. The flavour composition according to claim 4, wherein X represents ethylene or propylene, optionally substituted with one or more substituents selected from hydroxyl or methyl.

13. The flavour composition according to claim 5, wherein X represents ethylene or propylene, optionally substituted with one or more substituents selected from hydroxyl or methyl.

14. A product selected from the group consisting of foodstuffs, beverages, tobacco products and oral care products, comprising at least 0.1 ppm of a taste improving substance according to formula (I) as defined in claim 1, or edible salts thereof.

15. The product according to claim 14, wherein the taste improving substance is selected from the group consisting of N-(2-hydroxyethyl) 3-hydroxypropionamide; N-(2-hydroxyethyl) N-5-hydroxypentanoylamide; N-(2-hydroxyethyl) 4-hydroxypentanoylamide; N-(2-hydroxyethyl) 3-hydroxypentanoylamide; N-(2-hydroxyethyl) N-6-hydroxyhexanoylamide; N-(2-hydroxyethyl) 5-hydroxyhexanoylamide; N-(2-hydroxyethyl) 4-hydroxyhexanoylamide; N-(2-hydroxyethyl) 3-hydroxyhexanoylamide; N-(2-hydroxyethyl) 4-hydroxy-2-keto-3-methyl-pentanoylamide, and N-(2-hydroxyethyl) 4-hydroxy-2-keto-3-methyl-hexanoylamide.

16. A process for improving the taste of a foodstuff, a beverage, a tobacco product or an oral care product, comprising the step of adding to said foodstuff, beverage, tobacco product or oral care product a taste improving substance according to formula (I) as defined in claim 1, or edible salts thereof, in an amount of at least 0.1 ppm.

* * * * *

UNITED STATES PATENT AND TRADEMARK OFFICE
CERTIFICATE OF CORRECTION

| | | |
|---|---|---|
| PATENT NO. | : 8,691,311 B2 | Page 1 of 1 |
| APPLICATION NO. | : 13/605279 | |
| DATED | : April 8, 2014 | |
| INVENTOR(S) | : Visser et al. | |

It is certified that error appears in the above-identified patent and that said Letters Patent is hereby corrected as shown below:

On the title page, Column 2, Item [56] Other Publications, Line 3, delete "Kowskaja G." and insert -- Kowskaja --

In the Claims

Column 12, Lines 16-17, Claim 15, delete "pentanoylamide," and insert -- pentanoylamide; --

Signed and Sealed this
Twenty-ninth Day of July, 2014

Michelle K. Lee
*Deputy Director of the United States Patent and Trademark Office*